US011338112B2

(12) United States Patent
Hsu et al.

(10) Patent No.: US 11,338,112 B2
(45) Date of Patent: May 24, 2022

(54) DEVICES FOR MONITORING MOVEMENT OF A SECURED CATHETER DURING A PROCEDURE (71) Applicant: Cathaid, Inc., Augusta, GA (US)

(72) Inventors: George Hsu, Augusta, GA (US); Xiaoyu Alan Zheng, Rockville, MD (US)

(*) Notice: Subject to any disclaimer, the term of this patent is extended or adjusted under 35 U.S.C. 154(b) by 166 days.

(21) Appl. No.: 16/626,652

(22) PCT Filed: Jul. 2, 2018

(86) PCT No.: PCT/US2018/040572
§ 371 (c)(1),
(2) Date: Dec. 26, 2019

(87) PCT Pub. No.: WO2019/010119
PCT Pub. Date: Jan. 10, 2019

(65) Prior Publication Data
US 2020/0222669 A1    Jul. 16, 2020

Related U.S. Application Data (60) Provisional application No. 62/528,219, filed on Jul. 3, 2017.

(51) Int. Cl.
A61M 25/02        (2006.01)
(52) U.S. Cl.
CPC ..... A61M 25/02 (2013.01); A61M 2025/0246 (2013.01); A61M 2025/0266 (2013.01);
(Continued)
(58) Field of Classification Search
CPC ............ A61M 2025/0246; A61M 2025/0266; A61M 2025/0273; A61M 2205/33; A61M 25/02; A61M 2205/583
See application file for complete search history.

(56) References Cited

U.S. PATENT DOCUMENTS

| 5,068,886 | A | 11/1991 | Lavia |
| 8,439,873 | B1 | 5/2013 | Donovan |
| 2007/0043326 | A1 | 2/2007 | Navarro |
| 2012/0078167 | A1 | 3/2012 | Baker |
| 2013/0317368 | A1* | 11/2013 | Warren ............... A61B 5/0507 600/473 |

(Continued)

FOREIGN PATENT DOCUMENTS

| CN | 101743031 A | 6/2010 |
| CN | 104043188 A | 9/2014 |

(Continued)

OTHER PUBLICATIONS

International Search Report for PCT/US18/40572, dated Sep. 24, 2018.

(Continued)

Primary Examiner — Deanna K Hall
(74) Attorney, Agent, or Firm — Novel IP (57) ABSTRACT A device for securing and monitoring movement of a catheter includes a film having an adhesive disposed on a body-facing surface for securing the film to a body. The device also includes a base mounted on the film, the base comprising a first portion of a guide channel for receiving the catheter. A cover is coupled to the base via a hinge, the cover comprising a second portion of the guide channel, the cover further comprising a rounded portion extending from a distal end of the cover, wherein in the closed configuration, the catheter is completely enclosed by the rounded portion and the first and second portions of the guide channel. The device also includes a positional shift indicator fixedly attached to the catheter and configured to indicate positional shifts by the catheter within the guide channel.

22 Claims, 8 Drawing Sheets (52) U.S. Cl.
CPC ............... *A61M 2025/0273* (2013.01); *A61M 2205/0205* (2013.01); *A61M 2205/33* (2013.01); *A61M 2205/583* (2013.01)

(56) References Cited

U.S. PATENT DOCUMENTS

| | | |
|---|---|---|
| 2014/0066882 A1 | 3/2014 | Heinecke |
| 2016/0136395 A1 | 5/2016 | Hsu |
| 2016/0206855 A1 | 7/2016 | Howell |
| 2016/0256665 A1* | 9/2016 | Doshi .................... A61F 5/08 |
| 2017/0087336 A1 | 3/2017 | Chang |

FOREIGN PATENT DOCUMENTS

| | | | |
|---|---|---|---|
| CN | 104245033 | A | 12/2014 |
| CN | 105025969 | A | 11/2015 |
| CN | 106512179 | A | 3/2017 |
| CN | 106669010 | A | 5/2017 |
| JP | H10328310 | A | 12/1998 |
| KR | 20170031866 | A | 3/2017 |
| WO | 2013086099 | A1 | 6/2013 |
| WO | 2014149668 | A1 | 9/2014 |
| WO | 2016137872 | A1 | 9/2016 |
| WO | 2019010119 | A1 | 1/2019 |

OTHER PUBLICATIONS

Written Opinion of the International Searching Authority for PCT/US18/40572, dated Sep. 24, 2018.
International Preliminary Report on Patentability for PCT/US18/40572, dated Sep. 24, 2018.

* cited by examiner

DEVICES FOR MONITORING MOVEMENT OF A SECURED CATHETER DURING A PROCEDURE

CROSS-REFERENCE TO RELATED APPLICATION

The present application is a 371 National Stage application of PCT/US2018/040572, entitled "Device with Open Cutout Design for Securement and Position Verification of Medical Catheters" and filed on Jul. 2, 2018, which claims priority to, and the benefit of, U.S. Provisional Patent Application entitled, "Medical Devices for Placing and Securing Catheters," having Ser. No. 62/528,219, filed on Jul. 3, 2017, both of which are incorporated by reference in their entirety.

TECHNICAL FIELD

The present disclosure generally relates to medical devices and more particularly, to an antimicrobial, securement, and position verification device for medical catheters.

BACKGROUND

Medical catheters are invaluable tools in the medical field. However, infections associated with inadvertent positional shifts of catheters are a major source of morbidity and mortality for patients. Healthcare providers are also unable to assess positional changes in catheters without utilizing radiographic imaging. This exposes the patient to unnecessary radiation and is also financially costly. While devices exist that individually address catheter associated problems, the use of multiple devices is cumbersome and inefficient in the healthcare process.

SUMMARY

Briefly described, one embodiment, among others, is a device for securing and monitoring movement of a catheter. The device comprises a film having an adhesive disposed on a body-facing surface for securing the film to a body. The device also comprises a base mounted on the film, the base comprising a first portion of a guide channel for receiving the catheter, the base further comprising a tab member protruding from a side of the base. The device also comprises a hinge coupled to the base, the hinge extending along a longitudinal direction of the base. The device also comprises a cover coupled to the base via the hinge such that the cover is operable to pivot about the hinge from an open configuration to a closed configuration, the cover comprising a second portion of the guide channel, the cover further comprising a rounded portion extending from a distal end of the cover, wherein in the closed configuration, the catheter is completely enclosed by the rounded portion and the first and second portions of the guide channel. In the closed configuration, the cover and the base form a housing for securing the catheter, wherein an adhesive is disposed on the first and second portions of the guide channel for restricting movement of the catheter, wherein the cover further comprises a positional shift indicator fixedly attached to the catheter and configured to indicate positional shifts by the catheter within the guide channel, wherein the positional shift indicator comprises a plurality of segments arranged in a direction perpendicular to a longitudinal direction of the cover.

Another embodiment is a method for securing and monitoring movement of a catheter utilizing a device comprising a film, a base, and a cover coupled to the base via a hinge. The method comprises attaching the film to a body, the film having an adhesive disposed on a body-facing surface for securing the film to the body. The method further comprises inserting the catheter at a catheter entry point into a body and placing the catheter in a first portion of a guide channel in the base for receiving the catheter, the base further comprising a tab member protruding from a side of the base. The method further comprises pivoting the cover coupled to the base via the hinge such that the cover is placed into a closed configuration with respect to the base, the cover comprising a second portion of the guide channel, the cover further comprising a rounded portion extending from a distal end of the cover. In the closed configuration, the catheter is completely enclosed by the rounded portion and the first and second portions of the guide channel. In the closed configuration, the cover and the base form a housing for securing the catheter, wherein an adhesive is disposed on the first and second portions of the guide channel for restricting movement of the catheter, wherein the cover further comprises a positional shift indicator fixedly attached to the catheter and configured to indicate positional shifts by the catheter within the guide channel, wherein the positional shift indicator comprises a plurality of segments arranged in a direction perpendicular to a longitudinal direction of the cover.

Another embodiment is a device for securing and monitoring movement of a catheter. The device comprises an oval-shaped film having an adhesive disposed on a body-facing surface for securing the film to a body, the film having a cutout portion extending from an edge of the film to a central portion of the film. The device further comprises a tapered base mounted on the film, the base comprising a first portion of a guide channel for receiving the catheter, the base further comprising a rectangular tab member protruding from a side of the base. The device further comprises a hinge coupled to the base, the hinge extending along a longitudinal direction of the base. The device further comprises a tapered cover coupled to the base via the hinge such that the cover is operable to pivot about the hinge from an open configuration to a closed configuration, the cover comprising a second portion of the guide channel, the cover further comprising a semi-circular member extending from a distal end of the cover, wherein in the closed configuration, the catheter is completely enclosed by the semi-circular member and the first and second portions of the guide channel. In the closed configuration, the cover and the base form a housing for securing the catheter, wherein an adhesive is disposed on the first and second portions of the guide channel for restricting movement of the catheter, wherein the cover further comprises a positional shift indicator fixedly attached to the catheter and configured to indicate positional shifts by the catheter within the guide channel, wherein the positional shift indicator comprises a plurality of segments arranged in a direction perpendicular to a longitudinal direction of the cover.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Various aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Medical catheters are invaluable tools in the medical field. However, the use of catheters can present certain challenges. Typically, upon initial placement of a catheter, a healthcare provider applies an adjuvant antimicrobial barrier device at the site of catheter insertion. A secondary adjuvant device is then applied over the medical catheter to secure the catheter position. Significantly, the use of multiple adjuvant devices in conjunction with a medical catheter is inefficient and increases the risk of malfunction and subsequent harm to the patient. Furthermore, healthcare providers are unable to assess positional shifts of a medical catheter without utilizing a radiographic study, which is expensive and exposes the patient to unnecessary radiation.

Various embodiments are described for incorporating an improved securement device utilized in conjunction with medical catheters. By utilizing the device disclosed herein, healthcare providers are able to address the problems of catheter associated infections, catheter securement, and detection of inadvertent catheter positional shifts in a single device, thereby simplifying the utilization of a medical catheter. In accordance with various embodiments, the device is configured as a single adjuvant to medical catheters and attaches at the entry point of the catheter to the skin. For some embodiments, the device fully covers the catheter entry site while securing the catheter to prevent any positional shifts. Indicators are implemented on the device, which alert healthcare providers of any positional shifts by the catheter that may have occurred. Notably, a single device is disclosed that provides antimicrobial protection, securement against positional shifts, and the ability to alert healthcare providers of inadvertent positional shifts without the need for additional radiographic studies.

Figure 1:
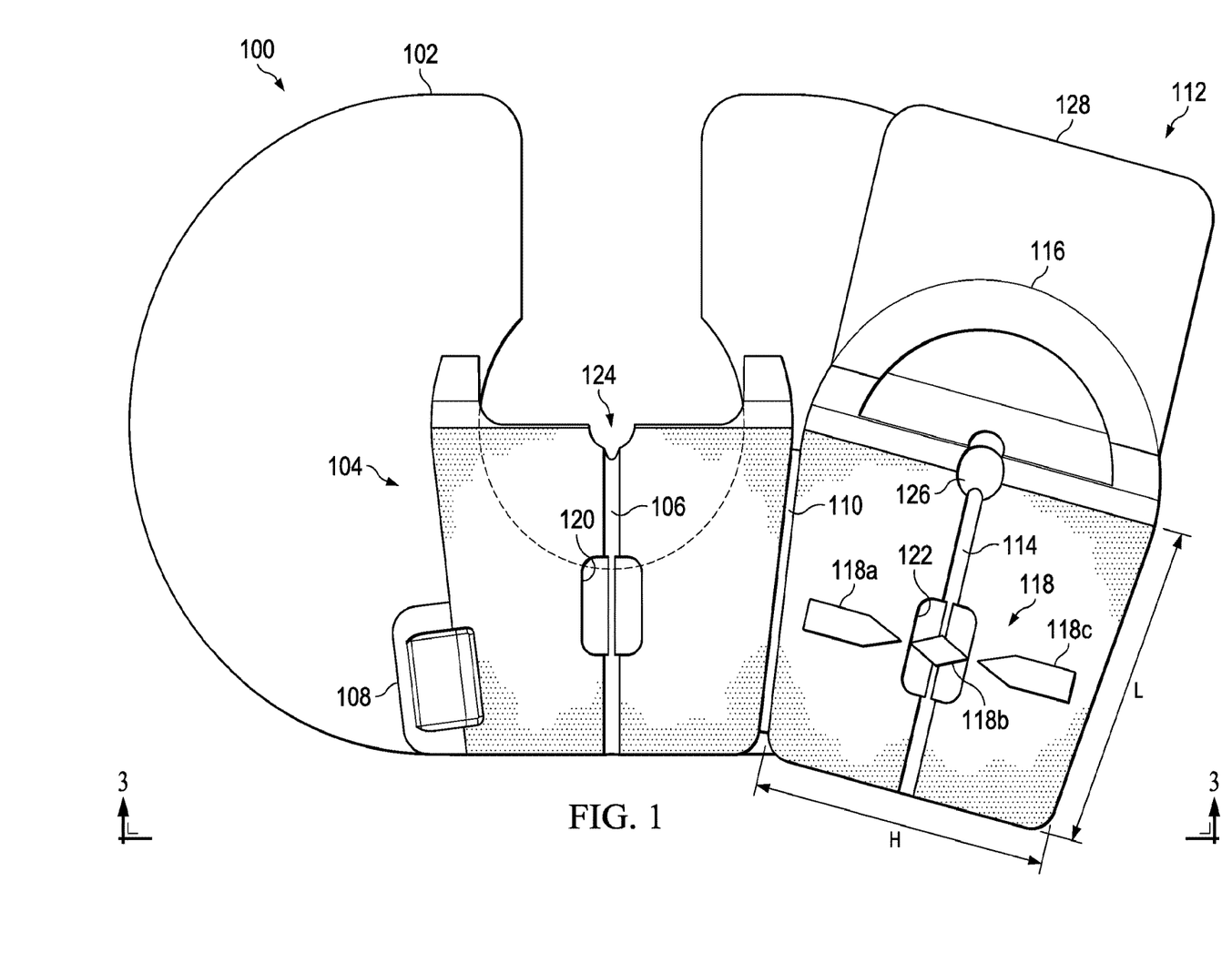
FIG. 1 illustrates a top plan view of the device while in an open configuration according to various embodiments.

Reference is made to FIG. 1, which illustrates a top plan view of the device 100 while in an open configuration according to various embodiments. The device 100 comprises a film 102 having an adhesive disposed on a body-facing surface for securing the film 102 to a body. For some embodiments, multiple components of the device 100 may have antimicrobial properties either intrinsically or coated with various antimicrobial substance. For example, the body-facing surface of the film 102 may have antimicrobial properties. The device 100 includes a base 104 mounted on the film 102, where the base 104 includes a first portion 106 of a guide channel for receiving a catheter. Specifically, a first portion 106 having a semi-circular cross section is formed in the base 104.

The device 100 further comprises a hinge 110 coupled to the base 104. A cover 112 is coupled to the base 104 via the hinge 110 such that the cover 112 is operable to pivot about the hinge 110 to transition from an open configuration to a closed configuration where the cover 112 comes in contact with the base 104. As shown, the base 104 further comprises a tab member 108 that protrudes from a side of the base 104. For some embodiments, the tab member 108 is a rectangular structure and is aligned with a bottom edge of the base 104. The tab member 108 facilitates initial application of the device 100 to the body by allowing a medical professional to press down on the tab member 108 while placing the device 100 into the closed configuration. The tab member 108 is also utilized to create a fulcrum to facilitate removal of the device 100.

For some embodiments, the cover 112 and the base 104 are each constructed of a clear medical grade silicone material. The cover 112 further comprises a second portion 114 of the guide channel. As with the first portion 106 of the guide channel in the base 104, the second portion 114 has a semi-circular cross section and is formed in the cover 112. In the closed configuration, the first portion 106 and the second portion 114 form a guide channel with a circular cross section for directing the catheter to a catheter entry point into the body. For some embodiments, the guide channel has a diameter that is approximately the same diameter of the catheter being inserted into the body. The guide channel is also operable for securing the catheter and alerting medical professionals of any positional shifts, as described in more detail below. For some embodiments, an adhesive is disposed on the first and second portions 106, 114 of the guide channel for restricting movement of the catheter.

Figure 2:
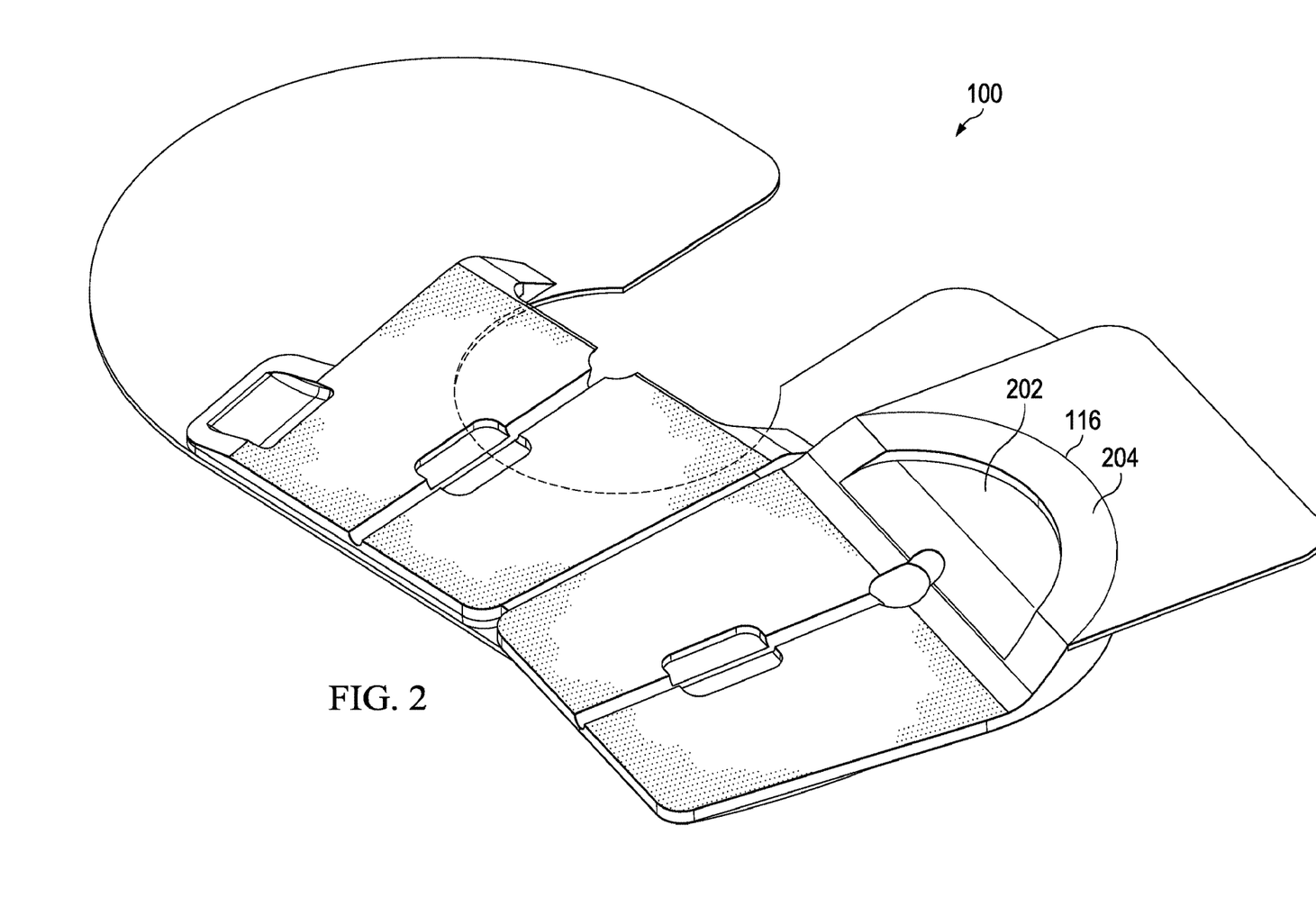
FIG. 2 illustrates a perspective view of the device in FIG. 1 according to various embodiments.
Figure 3:
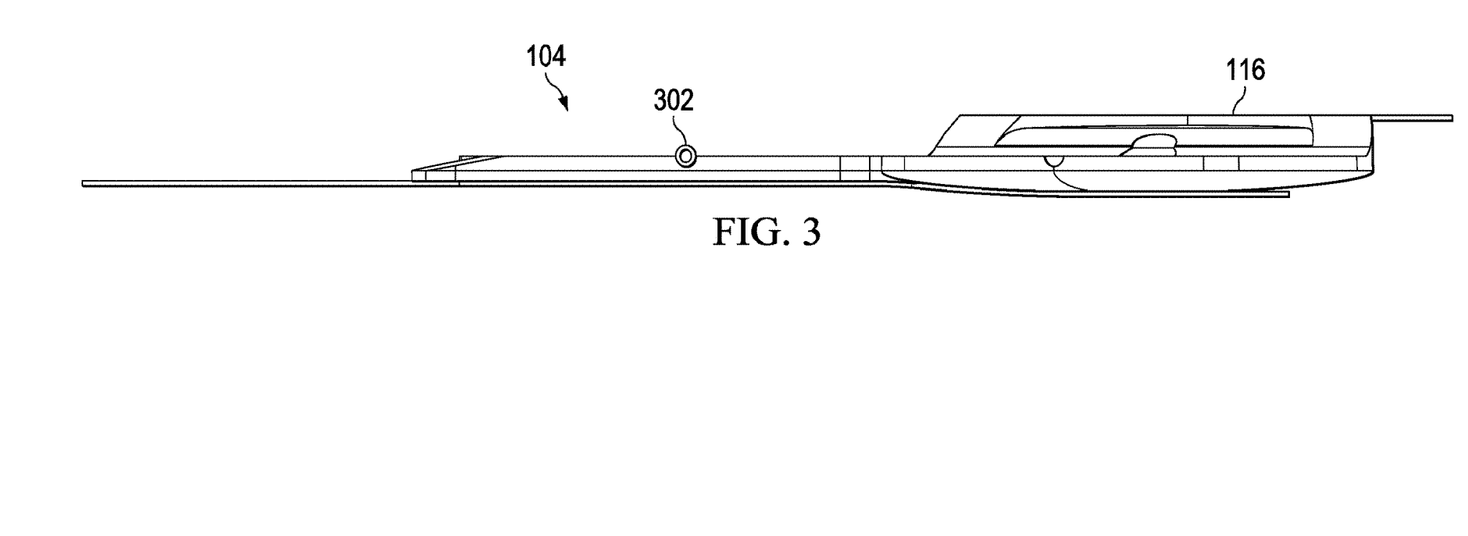
FIG. 3 illustrates a side view of the device in FIG. 1 in the direction of view arrows 3-3 while in an open configuration according to various embodiments.

The cover 112 further comprises a rounded portion 116 that extends from a distal end of the cover 112. FIG. 2 illustrates a perspective view of the device 100 while in an open configuration according to various embodiments. As shown, a recess region 202 is formed in the rounded portion 116 such that an outer c-shaped seal 204 is formed on the perimeter of the rounded portion 116. FIG. 3 illustrates a side view of the device 100 in FIG. 1 in the direction of view arrows 3-3 while in an open configuration. When placed in the closed configuration, the rounded portion 116 forms an enclosure with the base 104 such that the catheter 302 is completely enclosed by the rounded portion 116 and the first and second portions 106, 114 of the guide channel.

Referring back to FIG. 1, the cover 112 includes a positional shift indicator 118 configured to indicate positional shifts by the catheter within the guide channel where the positional shift indicator 118 is fixedly attached to the catheter. For some embodiments, the positional shift indicator 118 comprises multiple segments 118a, 118b, 118c, where the segments 118a, 118b, 118c are arranged in a side-by-side configuration extending in a lateral direction (H) of the cover 112. Specifically, the segments 118a, 118b, 118c are arranged in a direction perpendicular to a longitudinal direction (L) in which the second portion 114 of the guide channel extends in the cover 112. Note that the configuration of segments 118a, 118b, 118c may change depending on the intended application where the individual segments 118a,118b, 118c may be static or may move in relation to the catheter. Additionally the segments 118a, 118c adjacent to the center segment 118b may be placed in various configurations in relation to the adhesive film placed on the base 104 and the cover 112 depending on the intended application.

Figure 4:
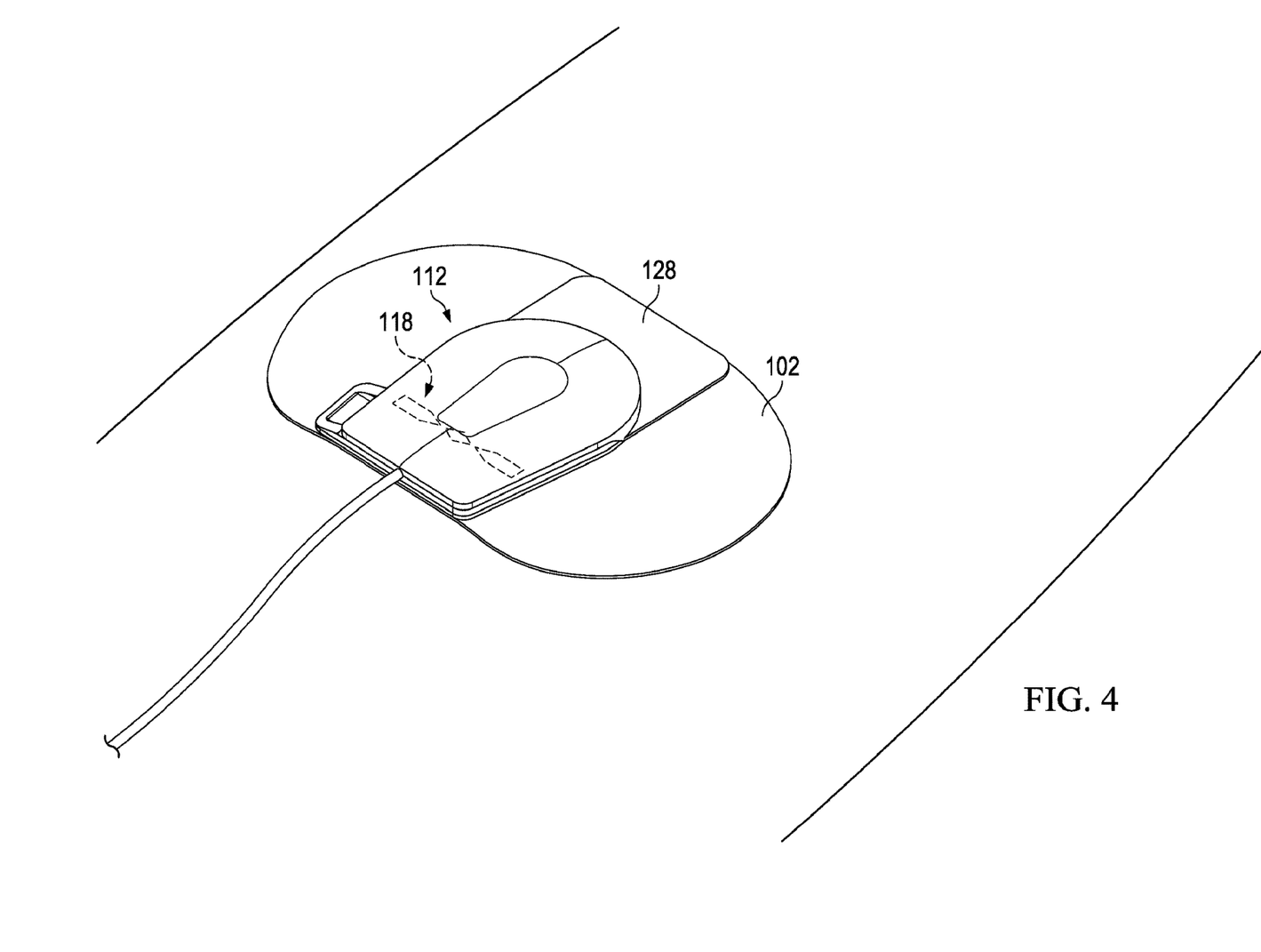
FIG. 4 illustrates a perspective view of the device in FIG. 1 while in a closed configuration according to various embodiments.

As shown, the first portion 106 of the guide channel in the base 104 includes a region 120 wider than a remainder of the first portion 106. Similarly, the second portion 114 of the guide channel in the cover 112 includes a region 122 wider than a remainder of the second portion 114. For some embodiments, one of the plurality of segments 118a, 118b, 118c is disposed within the region 122 of the second portion 114 in the cover. Specifically, a center segment 118b among the plurality of segments 118a, 118b, 118c may be disposed within the region 122 of the second portion 114, where the wider region 122 functions as a window for the positional shift indicator 118 and alerts medical professionals of any positional shifts in the catheter. FIG. 4 illustrates a perspective view of the device in FIG. 1 while in a closed configuration. Due to construction of the cover 112 from clear medical grade silicone or other suitable material, the positional shift indicator 118 attached to the catheter is viewable from a top view through a top surface of the cover 112 while the device 100 is in the closed configuration.

The device 100 may be constructed using medical grade silicone rubbers, plastics, fabrics, or other suitable materials. The type of antimicrobial substance used in the device 100 may also be varied to address specific microorganisms or conditions. It should be noted that the dimensions and orientation of individual or assembled components may be varied for use with different types of medical catheters. Similarly the positional shift indicator 118 may be altered to adapt to different types of catheters. Additionally, certain aspects of individual components can potentially be altered to meet dimensional or environmental conditions present during the usage of the catheter.

Referring back to FIG. 1, the first portion 106 of the guide channel in the base 104 includes a notch 124 at a distal end of the first portion 106 of the guide channel. The notch 124 functions as a catheter entry point for insertion of the catheter into the body. As shown, the notch 124 is disposed over a cutout portion of the film 102. The open cutout design of the film 102 is described in more detail below. The second portion 114 of the guide channel includes a recess 126 in the cover 112 at a distal end of the second portion 114. In the closed configuration, the recess 126 and the notch 124 allow the catheter to enter the body while the cover 112 forms a complete seal over the catheter.

The cover 112 further comprises a second film 128 having an adhesive disposed on a body-facing surface for securing the second film 128 to the body. The second film 128 is attached to and extends from the rounded portion 116 of the cover 112. As shown in FIG. 4, in the closed configuration, the second film 128 is disposed over the cutout region of the film 102 to form a complete seal around the catheter entry point into the body.

Figure 5:
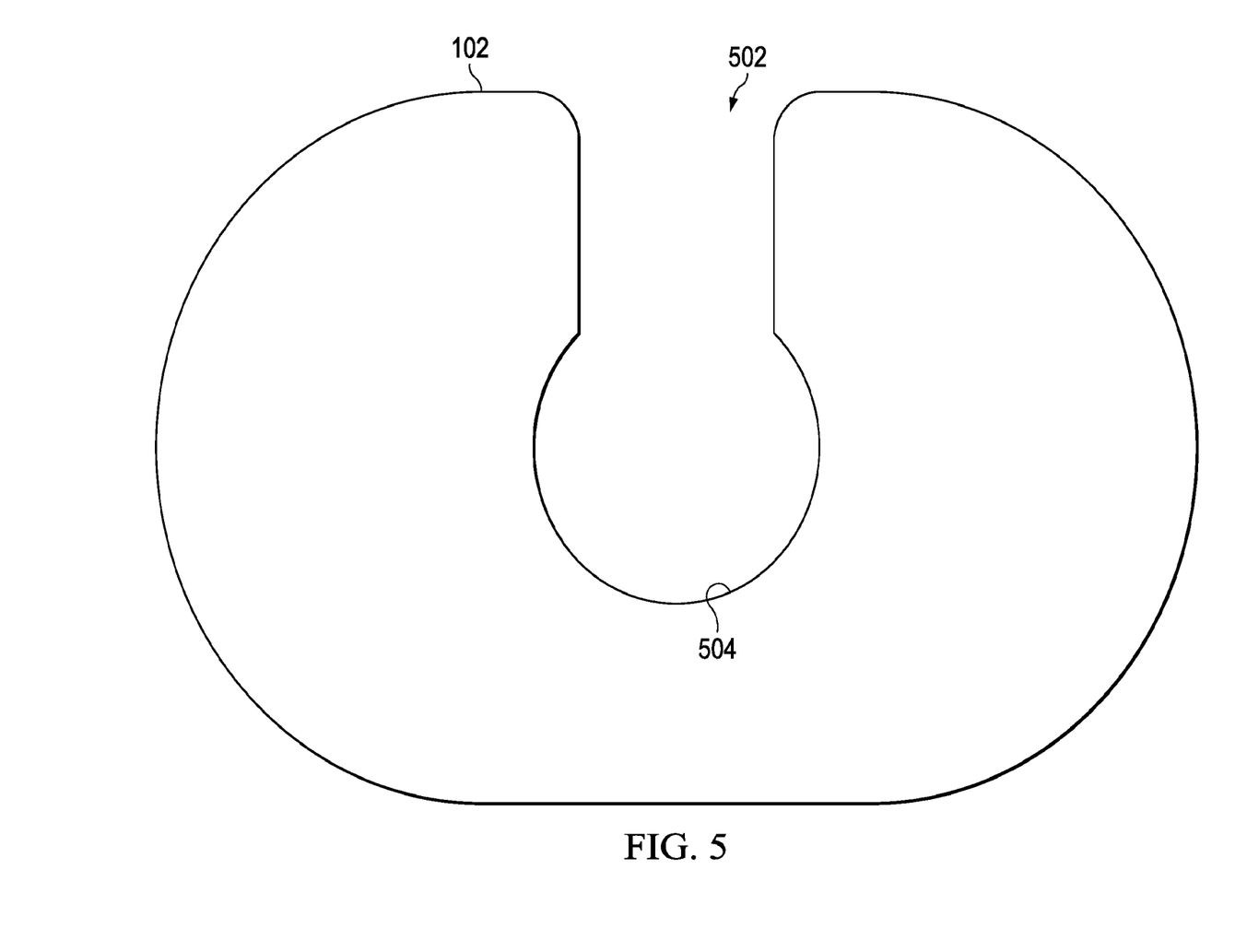
FIG. 5 illustrates a top plan view of the film of the device in FIG. 1 according to various embodiments.

FIG. 5 illustrates the open cutout design of the film 102 of FIG. 1. For some embodiments, the film 102 includes a cutout portion 502 that extends from an edge of the film to a central portion of the film 102. The circular region 504 of the cutout portion 502 allows a medical professional to apply dressing containing an antiseptic agent at the catheter entry point to reduce the possibility of infection. One advantage of the open cutout design of the film 102 is that this design allows a medical professional to easily insert the catheter through the guide channel of the device 100 (FIG. 1) and directly into the catheter entry point of the body while the device 100 is in the open configuration.

In contrast, a continuous film design (i.e., one where there is no cutout in the film) would require a medical professional to thread the catheter through a slit or hole cut in the film 102. Alternatively, the entire device 100 would have to be open on one side, thereby potentially exposing part of the catheter entry point. In contrast, the open cutout design of the film 102 allows for easy insertion of the catheter. In the closed configuration, the second film 128 (FIG. 1) and the rounded portion 116 (FIG. 1) of the cover 112 (FIG. 1) cover the cutout portion 502 of the film 102, thereby providing a complete seal around the catheter entry point.

Figure 6:
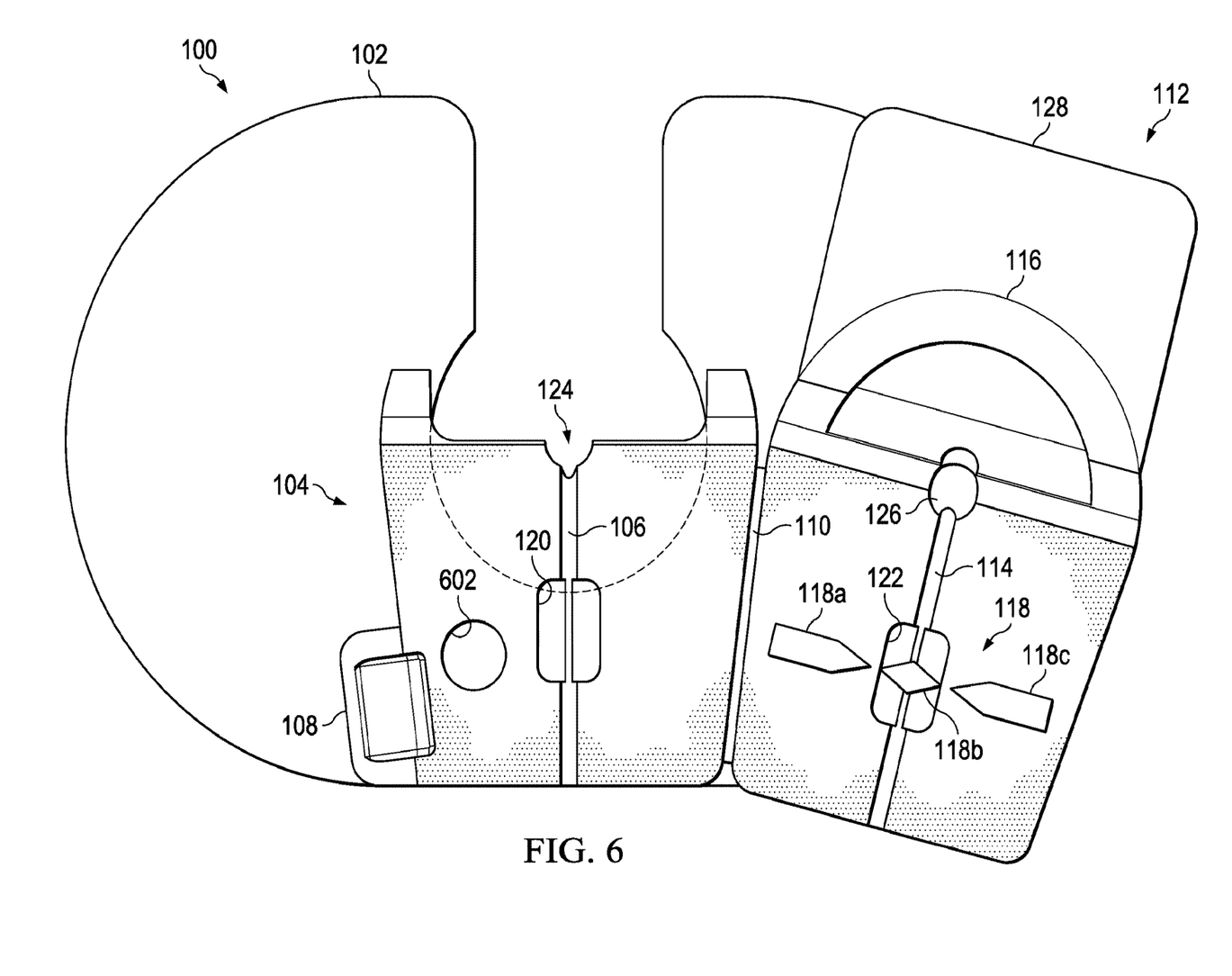
FIG. 6 illustrates a top plan view of an alternative embodiment of the device with a cutout in the base for insertion of a biomedical sensor according to various embodiments.
Figure 7:
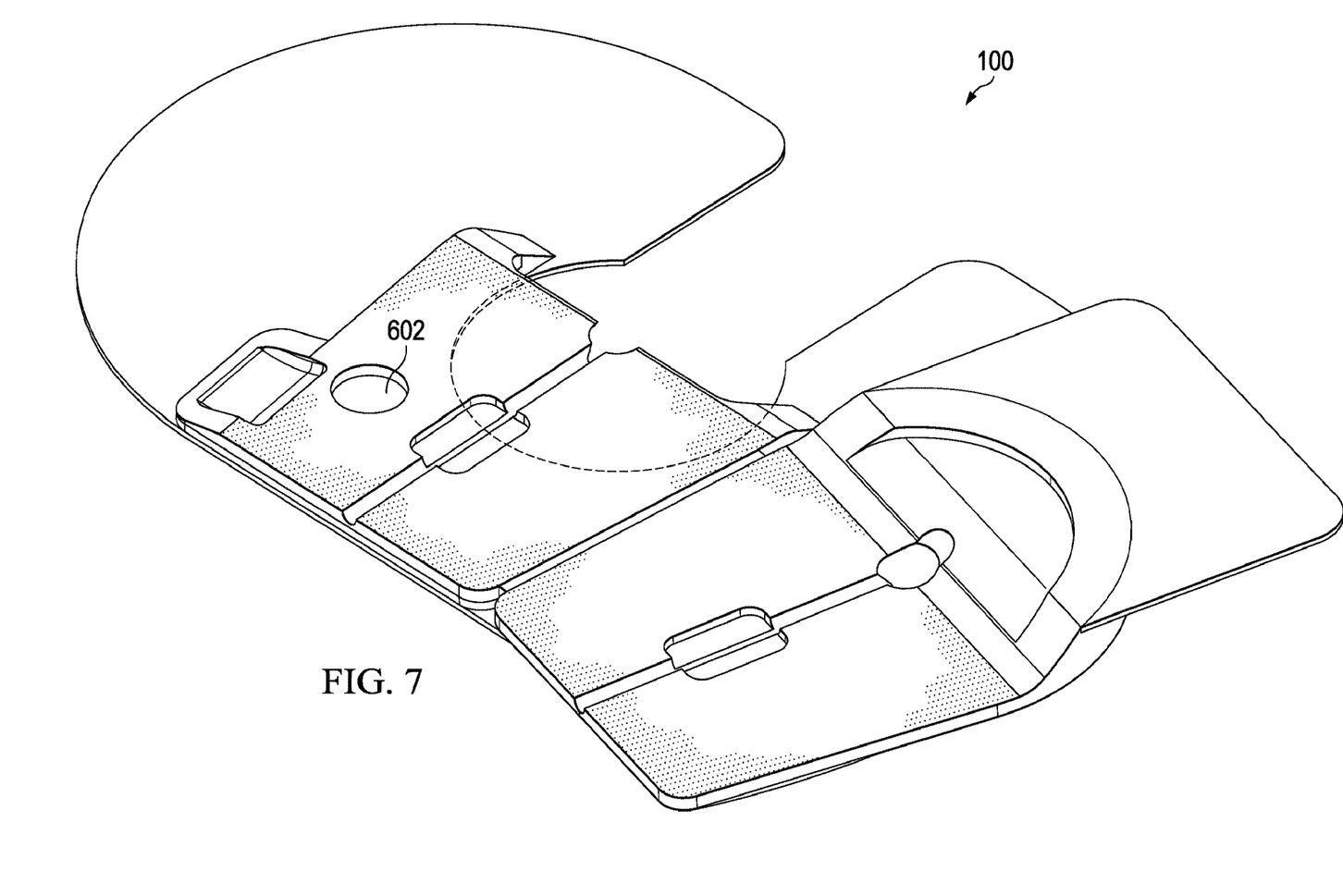
FIG. 7 illustrates a perspective view of the device in FIG. 6 according to various embodiments.

FIG. 6 illustrates a top plan view of an alternative embodiment of the device 100 with a recess 602 in the base 104 for insertion of a biomedical sensor (not shown) in the base 104 near the catheter entry point according to various embodiments. As shown in the perspective view provided in FIG. 7, the recess 602 in the base 104 may comprise a disc-shaped recess. For some embodiments, the recess 602 is embedded within the base 104 and is not accessible from the top surface of the base 104 that comes in contact with the cover 112. In other embodiments, however, the recess 602 is disposed on a top surface of the base 104 (as shown in FIG. 7). In this regard, the recess 602 may be disposed on the bottom surface of the base 104 where the sensor comes in contact with the skin or disposed on a top surface of the base 104. For other embodiments, the recess 602 may be disposed on either a top surface or a bottom surface of the cover 112. That is, the recess 602 can be disposed anywhere in either the base 104 or the cover 112, depending on the intended functionality of the sensor.

Note that although the FIG. 6 illustrates a disc-shaped recess 602 for placement of a biomedical sensor within the base 104, the recess 602 is not limited to this shape. Specifically, the shapes of the recess and the spatial relationship of the sensor in regard to the base 104 or cover 112 may vary depending on the intended sensor functionality. The sensor may be localized in a variety of locations within the device 100 depending on functionality of the sensor.

Due to the location of the recess 602 in the base 104, a biometric sensor may be placed proximal to the catheter entry site to facilitate detection of biofeedback signals relevant to catheter infection on proximal portion of the catheter. Such biofeedback signals may indicate, for example, temperature change, color change of the skin, detection of biologic antigens/chemical substances attributable to pathogenic organisms, and so on. A biometric sensor may be placed proximal to the catheter entry site to facilitate detection of biofeedback signals relevant to catheter dislodgement or movement where such biofeedback signals may comprise, for example, pressure signals, tension signals, kinematic signals, and so on. A biometric sensor may be placed proximal to the catheter entry site to facilitate detection of biofeedback signals relevant to catheter functionality of proximal portion of catheter where such biofeedback signals may comprise, for example, pressure signals, optical signals relevant to pulse-wave variations within the catheter, and so on. The biometric sensor may be isolated in functionality or may be part of a network of similarly connected monitors and/or feedback devices.

The biometric sensor used in conjunction with the device (FIG. 6) may include a variety of sensor types depending on the intended application. The biometric sensor can have stand-alone functionality or be potentially connected to other related Internet of things network. Sensors and integrated components can potentially collect a variety of data including skin and device temperature, skin and device color changes, skin and device moisture levels, presence or absence of specific healthcare related antigens/chemicals (e.g., microorganism bio products), motion and kinematic data, physiologic data, and so on. Additionally biometric sensors may collect data outside of information related to catheter functionality and in regards to the patient or environment as a whole.

Figure 8:
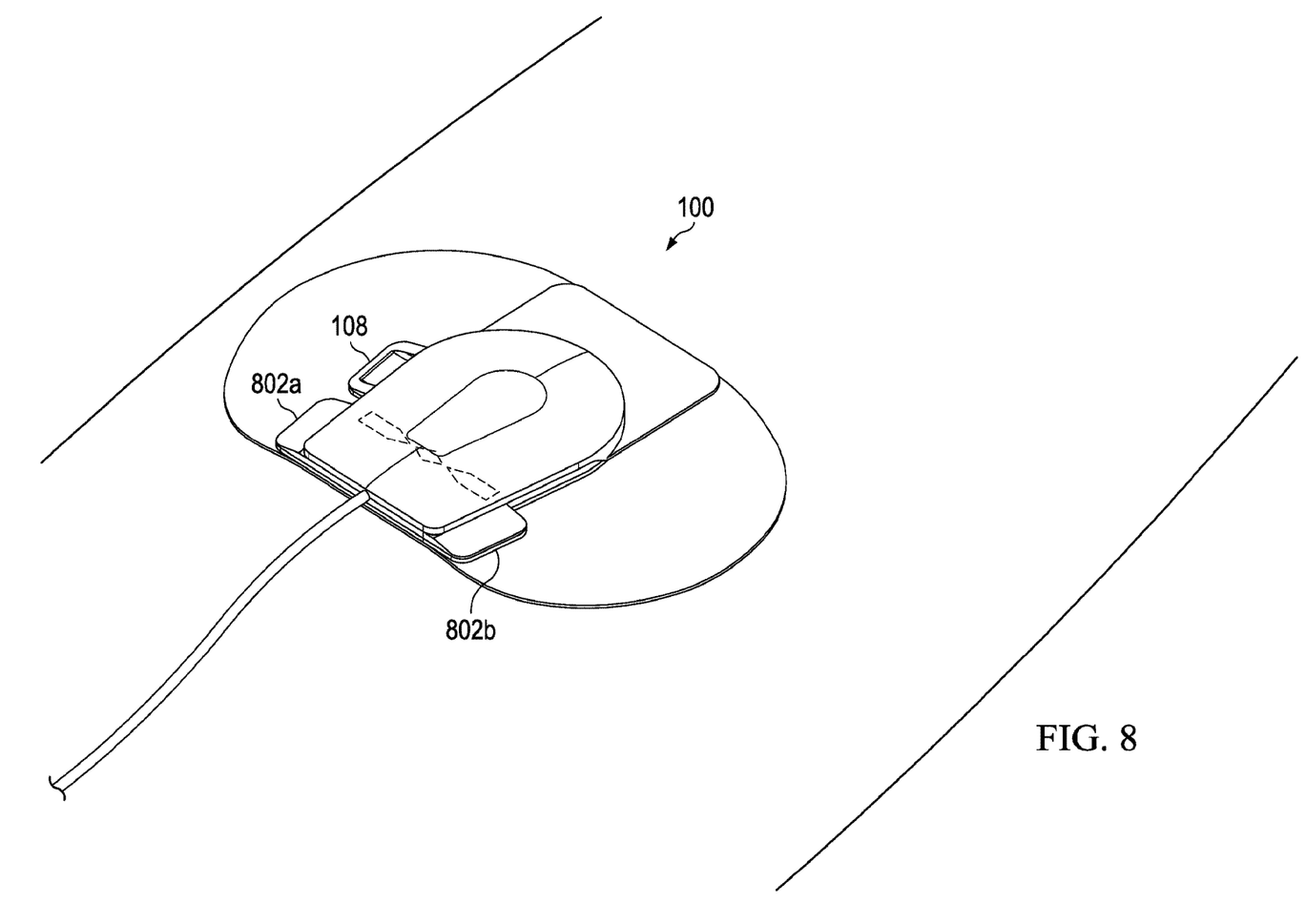
FIG. 8 illustrates a perspective view of an alternative embodiment of the device with stabilizer members in the base according to various embodiments.

FIG. 8 illustrates a perspective view of an alternative embodiment of the device 100 with stabilizers 802a, 802b in the base 104 of the device 100. The stabilizers 802a, 802b provide increased stabilization of the device 100 upon placement of the device 100 onto the body. The stabilizers 802a, 802b also facilitate correct parallel alignment between the catheter entry point and the body. Additionally the length of the stabilizers 802a, 802b may vary depending on the intended functionality of the device 100. For example, in cases where additional stabilization is needed, the stabilizers 802a, 802b may have increased length in proportion to the base 104. Corresponding components such as adhesives necessary to adhere the stabilizers 802a, 802b may also change depending on the intended use.

It should be emphasized that the above-described embodiments are merely examples of possible implementations. Many variations and modifications may be made to the above-described embodiments without departing from the principles of the present disclosure.

The invention claimed is:

1. A device configured to secure a catheter at an entry point to a body, comprising:
   a base having first and second opposing sides, wherein the first side has an adhesive and the second side has an area for receiving the catheter;
   a cover coupled to the base and configured to receive the catheter, wherein in a closed configuration the cover and the base form a housing for enclosing and securing at least a portion of the catheter;
   a first film attached to the cover with an adhesive disposed on a body-facing surface of the cover, wherein, in the closed configuration, the first film is disposed over the entry point to form a seal; and
   a positional shift indicator, wherein the positional shift indicator is physically coupled with the catheter after the catheter is received by the device, and wherein the positional shift is configured to visually indicate a degree of a positional shift of the catheter relative to the area and is adapted to be viewable through the cover.

2. The device of claim 1, wherein the area comprises a first portion of a guide channel for receiving the catheter.

3. The device of claim 2, wherein the cover comprises a second portion of the guide channel to receive the catheter.

4. The device of claim 3, wherein an adhesive is disposed on the first and second portions of the guide channel for restricting movement of the catheter.

5. The device of claim 1, wherein the cover is coupled to the base via a hinge such that the cover is operable to pivot about the hinge from an open configuration to the closed configuration.

6. The device of claim 1, wherein the cover further comprises a portion extending from a distal end of the cover.

7. The device of claim 1, wherein the positional shift indicator comprises a plurality of visible segments arranged in a direction perpendicular to a longitudinal direction of the cover.

8. The device of claim 1, further comprising first and second stabilizers in the base to facilitate correct parallel alignment between a catheter entry point and a body.

9. The device of claim 1, wherein the adhesive on the first side of the base is disposed on a body-facing surface of a second film attached to the first side.

10. The device of claim 1, wherein the positional shift indicator is physically coupled with the first side that when that first side is folded over onto the second side the positional shift indicator physically couples to the catheter.

11. A device configured for securing and monitoring movement of a catheter, comprising:
    a base having first and second opposing sides, wherein the first side has an adhesive and the second side has an area for receiving the catheter;
    a cover coupled to the base and configured to receive the catheter, wherein in a closed configuration the cover and the base form a housing for enclosing and securing at least a portion of the catheter;
    a positional shift indicator, wherein the positional shift indicator is physically coupled with the catheter after the catheter is received by the device and wherein the positional shift is configured to visually indicate a degree of a positional shift of the catheter relative to the area, and is adapted to be viewable through the cover; and
    a recess in the base for placement of a sensor proximate a catheter entry point into a body.

12. The device of claim 11, wherein the area comprises a first portion of a guide channel for receiving the catheter.

13. The device of claim 12, wherein the cover comprises a second portion of the guide channel to receive the catheter.

14. The device of claim 13, wherein an adhesive is disposed on the first and second portions of the guide channel for restricting movement of the catheter.

15. The device of claim 11, wherein the cover is coupled to the base via a hinge such that the cover is operable to pivot about the hinge from an open configuration to the closed configuration.

16. The device of claim 11, wherein the cover further comprises a portion extending from a distal end of the cover.

17. The device of claim 11, further comprising first and second stabilizers in the base to facilitate correct parallel alignment between the catheter entry point and the body.

18. The device of claim 11, further comprising the sensor, wherein the sensor is configured to detect signals related to at least one of an infection, a movement or a functionality of the catheter.

19. The device of claim 11, further comprising a first film attached to the cover with an adhesive disposed on a body-facing surface of the cover.

20. The device of claim 11, wherein the adhesive on the first side of the base is disposed on a body-facing surface of a second film attached to the first side.

21. The device of claim 11, wherein the positional shift indicator comprises a plurality of visible segments arranged in a direction perpendicular to a longitudinal direction of the cover.

22. The device of claim 11, wherein the positional shift indicator is physically coupled with the first side that when that first side is folded over onto the second side the positional shift indicator physically couples to the catheter.

* * * * *